United States Patent [19]

Subramanian et al.

[11] 4,032,625

[45] June 28, 1977

[54] BONE-SEEKING TECHNETIUM-99M COMPLEX

[75] Inventors: Gopal Subramanian, Manlius; John Gilmore McAfee, Fayetteville, both of N.Y.

[73] Assignee: Research Corporation, New York, N.Y.

[22] Filed: Mar. 26, 1975

[21] Appl. No.: 562,099

Related U.S. Application Data

[60] Division of Ser. No. 368,473, June 11, 1973, which is a continuation-in-part of Ser. No. 263,171, June 15, 1972, abandoned.

[52] U.S. Cl. .............................. 424/1; 252/301.1 R; 260/429 R
[51] Int. Cl.$^2$ ................ A61K 29/00; A61K 43/00; C07F 13/00
[58] Field of Search .................... 424/1; 252/301.1; 260/429

[56] References Cited

UNITED STATES PATENTS 3,735,001  5/1973  McRae et al. .......................... 424/1

OTHER PUBLICATIONS

Castronovo, Jr. et al., "New Bone Scanning Agent: $^{99m}$Tc–Labeled 1–Hydroxy–Ethylidene–1,1–Disodium Phosphonate," Journal of Nucleur Medicine, vol. 13, No. 11, Nov. 1972, pp. 823–827.

*Primary Examiner*—Benjamin R. Padgett
*Assistant Examiner*—Christine M. Nucker
*Attorney, Agent, or Firm*—Dennis P. Clarke

[57] ABSTRACT

A bone-seeking, technetium-99m-tin-phosphonate complex effective as a skeletal-imaging agent has been found particularly useful for diagnostic purposes. Skeletal tissue concentrations of technetium-99m obtained with the complex compare favorably to other bone-seeking radionuclides.

3 Claims, No Drawings

BONE-SEEKING TECHNETIUM-99M COMPLEX

BACKGROUND OF THE INVENTION

This is a division of application Ser. No. 368,473, filed June 11, 1973, which is a continuation-in-part application of Ser. No. 263,171, filed June 15, 1972, now abandoned.

This invention relates to a bone-seeking complex of technetium-99m.

Efforts to find a better gamma-emitting radionuclide for skeletal imaging to replace the long-lived nuclide strontium 85 (half-life 65 days) or inconveniently short-lived fluorine-18 (half-life 1.83 hours) have thus far been restricted mostly to the investigation of radioactive divalent alkaline earth cations, and the trivalent cations of gallium and the lanthanons. The excellent physical characteristics (half-life of 6 hours and monoenergetic gamma emission of 140 KeV with an external photon yield of 90%) of the readily available radionuclide technetium-99m are well-known. By virtue of its optimum half-life and absence of beta emission, technetium-99m can be administered in relatively large doses (10-15 mCi) without exceeding reasonable radiation levels. Until recently, technetium-99m has been used extensively in radioisotopic imaging procedures for almost every major organ in man with the exception of the skeleton.

In our copending application, Ser. No. 195,034 (filed Nov. 2, 1971) there is disclosed a metabolizable, bone-seeking composition comprising a technetium-99m-tin-polyphosphate complex prepared from a polyphosphate having a molecular weight above 300, preferably above 1400.

It was discovered that when solutions of technetium-99m-tin-polyphosphate complex are given intravenously, technetium-99m localizes to a great extent in bone, particularly in diseased or abnormal areas of the skeleton. Excellent visualization of both normal bone and skeletal lesions is observed about 2 hours after administration of the complex. Normal and abnormal skeletal tissue are readily delineated using conventional radioisotopes imaging devices such as rectilinear scanners or scintillation cameras.

It is an object of the invention to provide technetium-99m in additional bone-seeking forms suitable for use as skeletal-imaging agents.

SUMMARY OF THE INVENTION

The present invention is predicated on the discovery that when solutions of technetium-99m-tin-organodiphosphonate complexes are administered intravenously, technetium-99m localizes to a great extent in bone, particularly in diseased or abnormal areas of the skeleton. The presence of technetium-99m provides excellent visualization of both normal bone and skeletal lesions within about 2 hours after administration of the complex employing conventional radioisotope imaging devices such as rectilinear scanners or scintillation cameras.

DETAILED DESCRIPTION OF THE INVENTION

It has been reported that various diphosphonates exhibit the same inhibitory effect on calcification as polyphosphates at molar concentrations as low as $10^{-7}$ to $10^{-6}$. They have also been found to possess an affinity for hydroxyapatite crystals similar to that of polyphosphates. Diphosphonates have also been utilized in the treatment of osteoporosis. The following literature references report most of the work to date in the area of the administration of phosphonates to animals. [R. G. G. Russell et al, Calc. Tiss. Res., Vol. 6, pp. 183-196 (1970); M. E. Cabanela et al, Calc. Tiss. Res., Vol. 8, pp. 114-120 (1971); J. Jowsey et al, J. Lab. Clin. Med., Vol. 78, pp. 574-584 (1971); H. A. Fleisch et al, Europ. J. Clin. Invest., Vol. 1, pp. 12-18 (1970); R. G. G. Russell, Arch. Intern. Med., Vol. 124, pp. 571-577 (1969); M. D. Francis, Calc. Tiss. Res., Vol. 3, pp. 151-162 (1969); J. Jowsey et al, J. Lab. Clin. Med., Vol. 76, pp. 126-133 (1970)p; G. A. Nolen et al, Toxicology and App. Pharm. Vol. 18, pp. 548-561 (1971); and W. R. King et al, Clin. Orthop., Vol. 78, pp. 251-270 (1971)].

The diphosphonates employed in the practice of the invention are completely stable in vivo against chemical hydrolysis or hydrolysis by phosphatase enzymes thereby enhancing their value as a bone-seeking component in the composition and method of the invention.

The present invention is related to a bone-seeking composition comprising a technetium-99m-tin-organodiphosphonate complex. The present invention also contemplates methods for making the aforesaid complex, aqueous solutions containing the complex and methods for using the complex as a bone-seeking agent for skeletal-imaging.

Technetium-99m is commercially available either from an isotope generator as a daughter product of molybdenum-99 or as a direct product from a commercial supplier. It is also available as a solvent extraction product from molybdenum-99 solutions generally as alkali metal pertechnetate solutions at 5-100 mCi. A further discussion of preparative methods appears in U.S. Pat. Nos. 3,468,808 and 3,382,152.

Commercially available stannous salts, both hydrate and anhydrous, may be used as the tin source. Most readily available are stannous chloride, sulfate and acetate.

Suitable diphosphonates for forming the complexes of the present invention are well-known in the prior art. They and methods for their production are described in the above-noted publications and in Dutch Application No. 6,604,219 (Quimby et al, 1966). They may be utilized in the practice of the invention either as the free acid or as a non-toxic, pharmaceutically acceptable salt with a suitable cation such as sodium.

The preferred compounds are 1-hydroxy-ethane-1,1-diphosphonic, methylene diphosphonic, dichloromethylene diphosphonic, 1-amino-ethane-1,1-diphosphonic acids or their salts. The compounds formed by the polycondensation of the aforesaid compounds may also be utilized. The most preferred compound is methylene diphosphonic acid or its salts.

Suitable cations for forming the salts include sodium, potassium, magnesium, cesium, calcium, barium and iron. It is to be understood, however, that any non-toxic salt forming cation may be used.

The composition of the invention is most conveniently provided as a sterile kit consisting of non-radioactive chemicals for making with pertechnetate prior to use. The kit contains stannous salt solution, phosphonate solution, alkaline and/or buffer solution, or combinations of these. Using sterile pyrogen free water and reagents and using asectic techniques, these solutions would be mixed with each other and then with the pertechnetate solution. The particular order of mixing does not appear to be critical. Thus, the stannous salt could be added to the pertechenate solution and the mixture combined with the phosphonate solution. Alternatively, the phosphonate could be combined with the pertechnetate prior to the addition of the stannous salt or combined with the stannous salt and admixed with the pertechnetate.

One such kit involving the single step of adding pertechnetat to the other materials is prepared as follows:

EXAMPLE 1

750 Mg of 1-hydroxyethane-1,1-diphosphonate (EHDP) and 50 mg of stannous chloride ($SnCl_2$—$2H_2O$) (0.1 ml of 500 mg/ml of 5NHCL, freshly prepared) were dissolved in 30 ml of water. The pH was adjusted to 7.5 and the volume brought up to 50 ml. 2 Ml aliquots were pipetted into 20 vials and lyopholized overnight in conventional freeze-drying apparatus. Each of these "kits" contained 2 mg of $SnCl_2$—$2H_2O$ and 30 mg of DHDP (as acid). The complex was prepared by adding 4-6 ml (5-15 mc) of $99m_{Tc}$ as sodium pertechnetate to each of the vials and mixing well. The solutions were sterilized by passage through a 0.22 size membrane filter. The final pH ranged from 6.8 to 7.2. The solutions are now ready for intravenous injection.

The complexes of the invention were utilized as skeletal imaging agents in accordance with the following procedure.

chloride administered simultaneously. Each dosage is contained in a volume of 1 ml.

The animals were sacrificed serially from 1 to 24 hours after injection and the activities in major organs were determined by counting multiple samples from each organ in a scintillation well counter (the technetium-99m counts were corrected for the Compton contributions from the strontium-85 activity in the technetium-99m energy window). Multiple samples were counted from the tibia, femur, spine and pelvic bones; the total activity in the skeleton was estimated by assuming the whole skeleton consisted of equal proportions by weight of tibia, spine, femur and pelvis and that the skeletal mass was 10% of the body weight. The red marrow was sampled from the femur and the total marrow was assumed to be 2.2% of the total body weight. Similarly, blood volume was assumed to be 7% and the skeletal muscle 43% of the body weight. The whole liver and both kidneys were weighed and multiple samples from each were counted to measure the total activity in each organ.

In another series of experiments carried out as described above, localization of technetium from its tin-phosphonate complex was determined in the callous of three week-old fractures of tibia in albino rabbits, again in comparison with strontium-85. Comparative radioassay of technetium-99m administered as the pertechnetate was measured in the callous of tibial fractures in rabbits at one and four hours after administration. The results are set forth in Table 1.

TABLE 1

| DISTRIBUTION OF $99m$Tc-EHDP and $85$Sr IN RABBITS SIMULTANEOUS STUDY (6 EACH) | | | | | | | | |
|---|---|---|---|---|---|---|---|---|
| | % dose in whole organ | | | | | | | |
| | 1 Hr | | 2 Hrs | | 4 Hrs | | 24 Hrs | |
| ORGAN | $99m$Tc | $85$Sr | $99m$Tc | $85$Sr | $99m$Tc | $85$Sr | $99m$Tc | $85$Sr |
| Blood* | 8.61 | 11.9 | 2.58 | 7.08 | 0.89 | 3.85 | 0.49 | 0.29 |
| Liver | 0.80 | 1.57 | 0.42 | 0.98 | 0.28 | 0.62 | 0.43 | 0.04 |
| Muscle** | 6.46 | 13.4 | 1.82 | 8.8 | 1.25 | 6.46 | 0.87 | 1.00 |
| Kidneys | 2.40 | 0.80 | 1.22 | 0.64 | 0.94 | 0.34 | 0.63 | 0.03 |
| Marrow+ | 0.70 | 0.91 | 0.38 | 0.76 | 0.83 | 0.50 | 0.42 | 0.10 |
| One Femur | 0.82 | 1.04 | 0.84 | 1.21 | 0.81 | 1.25 | 0.76 | 0.93 |
| Bone(Avg)++ | 46.6 | 56.0 | 48.2 | 49.4 | 47.4 | 68.1 | 41.5 | 51.9 |
| Urine | 30.9 | 6.96 | 51.8 | 18.0 | 53.4 | 22.7 | — | — |
| | % dose / 1% body weight | | | | | | | |
| Blood | 1.23 | 1.70 | 0.37 | 1.01 | 0.13 | 0.55 | 0.07 | 0.04 |
| Liver | 0.30 | 0.59 | 0.18 | 0.43 | 0.11 | 0.26 | 0.28 | 0.02 |
| Muscle | 0.15 | 0.31 | 0.04 | 0.21 | 0.03 | 0.15 | 0.02 | 0.02 |
| Kidneys | 3.93 | 1.75 | 2.72 | 1.40 | 1.95 | 0.71 | 1.29 | 0.06 |
| Marrow | 0.36 | 0.41 | 0.17 | 0.34 | 0.38 | 0.23 | 0.19 | 0.05 |
| Bone(Avg) | 4.66 | 5.60 | 4.82 | 6.44 | 4.74 | 6.81 | 4.14 | 5.21 |
| Femur | 3.85 | 4.90 | 3.94 | 5.74 | 3.86 | 6.17 | 3.42 | 4.83 |
| Tibia | 2.17 | 3.62 | 2.49 | 4.73 | 2.16 | 5.13 | 2.10 | 4.27 |
| Pelvis | 7.15 | 7.07 | 7.40 | 7.70 | 7.41 | 8.02 | 5.70 | 5.26 |
| Spine | 5.87 | 7.03 | 5.44 | 7.59 | 5.52 | 7.82 | 5.30 | 6.47 |
| Callus | 24.7 | 31.2 | — | — | 28.9 | 37.7 | — | — |
| | RATIOS | | | | | | | |
| Bone/Blood | 4.3 | 3.4 | 14 | 6.4 | 38 | 13 | 81 | 134 |
| Bone/Marrow | 14 | 14 | 28 | 19 | 27 | 32 | 29 | 119 |
| One/Muscle | 35 | 19 | 123 | 32 | 196 | 47 | 292 | 227 |
| Plus/Blood | 20 | 18 | — | — | 225 | 81 | | |
| Plus/N. Tibia | 11 | 9 | — | — | 12 | 8 | | |
| Plus/N. Femur | 7 | 7 | — | — | 7 | 7 | | |

*7% of body weight
**43% of body weight
+2.2% of body weight
++10% of body weight

EXAMPLE 2

Adult New Zealand albino rabbits having an average weight of 3.8 kg were utilized. Strontium-85 was employed as a standard for comparison. In a typical experiment 20-250 μCi (i.e., containing approximately 1 mg/kg as the free acid of body weight) of $99M_{Tc}$ EHDP were injected intravenously into the rabbits through the marginal ear vein and compared with 10-20 μ Ci $85_{Sr}$ As is apparent from Table 1, the soft tissue and blood concentrations of the $99m_{Tc}$ EHDP at various times were much lower than those for $85_{Sr}$ whereas the skeletal concentrations were similar. The cumulative urinary excretion for $99m_{Tc}$ EHDP was at least 3 times higher than for $85_{Sr}$. The concentration of the $99m_{Tc}$ compound in the callous was somewhat lower than that of $85_{Sr}$; however, the callous normal bone concentration ratios were similar.

Imaging of the skeleton of albino rabbits with 3 week old tibial fractures after injection with the complexes of the invention as described in Example 2 was performed using a scintillation camera (Nuclear Chicago Pho-Gamma HP Camera with high sensitivity collinator for $99m_{Tc}$). Camera images of the entire body were obtained in three exposures and demonstrated the localization of Tc-99m in the callous of the fracture at 1, 2, 4 and 24 hours. The test demonstrated that very good skeletal images can be obtained any time beyond 2 hours after injection.

A total body scan or a normal dog after injection with the complexes of the invention as described in Example 2 utilizing a rectilinear scanner (OHio-Nuclear Model 84-D Scanner) was obtained 2 hours after injection at the $99m_{Tc}$ EHDP complex.

EXAMPLE 3

In another series of experiments carried out as described in Example 2, the distribution of technetium 99m from its 99m-technetium-tin-methylene diphosphonate complex was determined in albino rabbits, again in comparison with strontium-85. Comparative radioassay of technetium 99m were measured after 2 hours at the dosages indicated in Table 2. The results are set forth in Tables 2 and 3.

TABLE 2

CARRIER EFFECT OF MDP ON $^{99m}$TcMDP and $^{85}$Sr IN RABBITS, 2 Hrs. (6 each)

| Organ | 0.01 mg/kg | | 0.05 mg/kg | | 0.1 mg/kg | | 0.5 mg/kg | |
|---|---|---|---|---|---|---|---|---|
| | $^{99m}$Tc | $^{85}$Sr | $^{99m}$Tc | $^{85}$Sr | $^{99m}$Tc | $^{85}$Sr | $^{99m}$Tc | $^{85}$Sr |
| % Dose in Whole Organ | | | | | | | | |
| Blood | 1.12 | 3.27 | 0.92 | 3.66 | 0.91 | 3.95 | 0.83 | 3.1 |
| Liver | 0.45 | 0.65 | 0.36 | 0.71 | 0.37 | 1.05 | 2.41 | 0.69 |
| Kidneys | 1.24 | 0.34 | 2.58 | 0.46 | 1.70 | 0.66 | 0.99 | 0.45 |
| Marrow | 0.31 | 0.53 | 0.34 | 0.53 | 0.28 | 0.57 | 1.32 | 0.67 |
| One Femur | 2.45 | 3.46 | 2.35 | 2.53 | 2.46 | 2.80 | 2.35 | 2.96 |
| Muscle | 0.93 | 5.69 | 1.15 | 5.89 | 1.53 | 9.32 | 2.03 | 5.65 |
| Urine | 43.6 | 10.3 | 40.5 | 23.16 | 43.5 | 15.4 | 41.1 | 15.16 |
| % Dose/1% - body weight | | | | | | | | |
| Blood | 0.16 | 0.47 | 0.13 | 0.52 | 0.13 | 0.56 | 0.12 | 0.45 |
| Liver | 0.11 | 0.16 | 0.11 | 0.22 | 0.11 | 0.30 | 0.76 | 0.23 |
| Kidneys | 2.08 | 0.54 | 5.39 | 0.9 | 2.43 | 1.00 | 1.53 | 0.69 |
| Marrow | 0.14 | 0.24 | 0.16 | 0.24 | 0.13 | 0.26 | 0.60 | 0.30 |
| Femur | 9.87 | 13.93 | 8.24 | 9.10 | 8.77 | 10.0 | 9.58 | 11.32 |
| Tibia | 4.03 | 7.14 | 3.76 | 4.94 | 4.06 | 6.05 | 4.18 | 6.16 |
| Pelvis | 10.71 | 13.55 | 9.09 | 8.33 | 13.0 | 12.2 | 7.47 | 8.68 |
| Spine | 9.17 | 12.78 | 6.39 | 6.75 | 7.44 | 8.45 | 7.51 | 8.92 |
| Muscle | 0.02 | 0.13 | 0.03 | 0.14 | 0.03 | 0.22 | 0.05 | 0.13 |
| Ave Bone | 8.45 | 11.85 | 6.87 | 7.29 | 8.32 | 9.17 | 7.19 | 8.77 |
| $^{99m}$Tc/$^{85}$Sr | 0.713 | | 0.942 | | 0.907 | | 0.820 | |

TABLE 3

| | Ratio of $^{99m}$TcMDP/$^{85}$Sr | | | |
|---|---|---|---|---|
| Organ | 0.01 mg/kg | 0.05 mg/kg | 0.1 mg/kg | 0.5 mg/kg |
| Blood | 0.342 | 0.254 | 0.229 | 0.279 |
| Liver | 0.708 | 0.519 | 0.395 | 3.48 |
| Kidneys | 3.87 | 5.64 | 2.34 | 2.25 |
| Marrow | 0.576 | 0.648 | 0.519 | 2.51 |
| Femur | 0.709 | 0.963 | 0.922 | 0.866 |
| Tibia | 0.564 | 0.812 | 0.716 | 0.640 |
| Pelvis | 0.791 | 1.19 | 1.08 | 0.861 |
| Spine | 0.718 | 0.955 | 0.915 | 0.855 |
| Muscle | 0.159 | 0.193 | 0.150 | 0.401 |
| Ave Bone | 0.714 | 1.01 | 0.941 | 0.831 |

EXAMPLE 4

The distribution of technetium 99m from its 99m technetium-tin-1-amino-ethane-1,1-diphosphonate complex was determined as in Example 3 and compared with the distribution of strontium-85. The dosages and results are set forth in Tables 4 and 5 below.

TABLE 4

DISTRIBUTION OF $^{99m}$Tc-Sn-AEDP and $^{85}$Sr IN RABBITS (6 each) 2 Hrs. Carrier Effect of AEDP

| Organ | 0.01 mg/kg | | 0.05 mg/kg | | 0.1 mg/kg | | 0.5 mg/kg | |
|---|---|---|---|---|---|---|---|---|
| | $^{99m}$Tc | $^{85}$Sr | $^{99m}$TC | $^{85}$Sr | $^{99m}$Tc | $^{85}$Sr | $^{99m}$Tc | $^{85}$Sr |
| % Dose in Whole Organ | | | | | | | | |
| Blood | 1.18 | 2.99 | 1.01 | 2.50 | 0.96 | 2.48 | 1.38 | 4.36 |
| Liver | 1.69 | 0.568 | 0.806 | 0.613 | 0.309 | 0.654 | 0.216 | 0.720 |
| Kidneys | 1.59 | 0.329 | 1.13 | 0.353 | 0.913 | 0.324 | 1.11 | 0.384 |
| Marrow | 0.657 | 0.465 | 0.549 | 0.486 | 0.211 | 0.244 | 0.23 | 0.456 |
| W. Femur | 2.34 | 3.22 | 2.41 | 3.51 | 2.38 | 3.27 | 1.74 | 2.75 |
| W. Tibia | 1.96 | 2.71 | 2.14 | 3.15 | 2.18 | 2.99 | 1.55 | 2.42 |
| Muscle | 0.988 | 4.98 | 1.20 | 5.09 | 1.46 | 5.15 | 0.883 | 6.51 |
| Urine | 48.39 | 20.97 | 44.21 | 11.95 | 38.8 | 12.1 | 48.85 | 10.47 |
| % Dose/1% Body weight | | | | | | | | |
| Blood | 0.168 | 0.427 | 0.144 | 0.357 | 0.137 | 0.354 | 0.197 | 0.624 |
| Liver | 0.617 | 0.177 | 0.176 | 0.134 | 0.083 | 0.182 | 0.079 | 0.270 |
| Kidneys | 2.72 | 0.567 | 1.83 | 0.551 | 1.28 | 0.441 | 2.11 | 0.924 |
| Marrow | 0.300 | 0.211 | 0.250 | 0.221 | 0.096 | 0.166 | 0.104 | 0.207 |
| Femur | 7.54 | 10.38 | 8.63 | 12.62 | 7.93 | 10.97 | 6.59 | 10.43 |
| Tibia | 8.13 | 11.28 | 9.30 | 13.69 | 8.50 | 11.71 | 7.27 | 11.37 |
| Pelvis | 8.53 | 10.66 | 7.82 | 11.44 | 6.24 | 8.66 | 7.93 | 11.42 |
| Spine | 6.20 | 8.98 | 7.80 | 11.60 | 7.36 | 10.56 | 6.05 | 9.87 |

TABLE 4-continued

DISTRIBUTION OF $^{99m}$Tc-Sn-AEDP and $^{85}$Sr IN RABBITS (6 each)
2 Hrs. Carrier Effect of AEDP

| Organ | 0.01 mg/kg | | 0.05 mg/kg | | 0.1 mg/kg | | 0.5 mg/kg | |
|---|---|---|---|---|---|---|---|---|
| | $^{99m}$Tc | $^{85}$Sr | $^{99m}$TC | $^{85}$Sr | $^{99m}$Tc | $^{85}$Sr | $^{99m}$Tc | $^{85}$Sr |
| Bone Ave | 7.60 | 10.33 | 8.39 | 12.34 | 7.51 | 10.48 | 6.96 | 10.78 |
| Muscle | 0.037 | 0.116 | 0.028 | 0.118 | 0.034 | 0.136 | 0.021 | 0.151 |
| Tc/Sr | 0.736 | | 0.680 | | 0.717 | | 0.645 | |

TABLE 5

| | Ratio of $^{99m}$Tc/$^{85}$Sr | | | |
|---|---|---|---|---|
| Organ | 0.01 mg/kg | 0.05 mg/kg | 0.1 mg/kg | 0.5 mg/kg |
| Blood | 0.406 | 0.409 | 0.409 | 0.280 |
| Liver | 3.00 | 1.32 | 0.490 | 0.459 |
| Kidney | 4.99 | 3.30 | 2.94 | 2.47 |
| Marrow | 1.27 | 1.18 | 0.621 | 0.500 |
| Femur | 0.720 | 0.687 | 0.714 | 0.628 |
| Tibia | 0.710 | 0.681 | 0.721 | 0.632 |
| Pelvis | 0.794 | 0.684 | 0.725 | 0.692 |
| Spine | 0.689 | 0.675 | 0.705 | 0.614 |
| Ave Bone | 0.735 | 0.683 | 0.716 | 0.644 |
| Muscle | 0.338 | 0.236 | 0.205 | 0.140 |

EXAMPLE 5

Another set of experiments were carried out according to the method of Example 2 but varying the dosages as in Examples 3 and 4. The distribution of technetium 99m from its tin-1-hydroxy-ethane-1,1-diphosphonate after 2 hours was determined and compared with the distribution of strontium 85 from equivalent dosages. The dosages and results are set forth in Tables 6 and 7 below.

TABLE 6

DISTRIBUTION OF $^{99m}$Tc-Sn-EHDP and $^{85}$Sr IN RABBITS (6 each)
Carrier Effect of EHDP, 2 Hrs.

| Organ | 0.01 mg/kg | | 0.05 mg/kg | | 0.1 mg/kg | | 0.5 mg/kg | |
|---|---|---|---|---|---|---|---|---|
| | $^{99m}$Tc | $^{85}$Sr | $^{99m}$Tc | $^{85}$Sr | $^{99m}$Tc | $^{85}$Sr | $^{99m}$Tc | $^{85}$Sr |
| % Dose in Whole Organ | | | | | | | | |
| Blood | 0.99 | 3.19 | 1.35 | 3.39 | 1.02 | 3.10 | 1.503 | 4.43 |
| Liver | 0.53 | 0.74 | 1.61 | 0.77 | 0.19 | 0.64 | 0.260 | 0.76 |
| Kidneys | 0.81 | 0.43 | 2.9 | 0.46 | 0.63 | 0.30 | 1.10 | 0.48 |
| Marrow | 0.34 | 0.42 | 0.78 | 0.61 | 0.20 | 0.43 | 0.19 | 0.34 |
| One Femur | 2.20 | 2.83 | 2.44 | 3.33 | 2.82 | 3.42 | 1.75 | 2.48 |
| One Tibia | 2.05 | 2.60 | 2.22 | 3.04 | 2.44 | 2.98 | 1.43 | 2.07 |
| Muscle | 0.78 | 5.78 | 1.33 | 6.64 | 0.98 | 5.0 | 1.22 | 7.23 |
| Urine | 46.7 | 23.66 | 37.3 | 13.4 | 30.4 | 11.31 | 55.37 | 19.67 |
| % Dose/1%-body weight | | | | | | | | |
| Blood | 0.142 | 0.456 | 0.193 | 0.485 | 0.146 | 0.443 | 0.215 | 0.633 |
| Liver | 0.154 | 0.206 | 0.432 | 0.210 | 0.068 | 0.230 | 0.086 | 0.244 |
| Kidney | 1.55 | 0.655 | 3.83 | 0.616 | 1.09 | 0.513 | 2.23 | 0.972 |
| Marrow | 0.152 | 0.192 | 0.353 | 0.291 | 0.093 | 0.195 | 0.088 | 0.152 |
| Femur | 7.49 | 9.70 | 8.38 | 11.51 | 8.97 | 10.9 | 6.487 | 9.213 |
| Tibia | 8.22 | 10.47 | 8.68 | 11.93 | 9.63 | 11.89 | 6.639 | 9.02 |
| Pelvis | 7.57 | 9.06 | 8.25 | 10.50 | 12.10 | 13.62 | 7.38 | 9.44 |
| Spine | 6.17 | 8.39 | 6.51 | 9.13 | 8.18 | 10.75 | 5.885 | 8.69 |
| Muscle | 0.018 | 0.135 | 0.031 | 0.154 | 0.023 | 0.116 | 0.028 | 0.168 |
| Ave Bone | 7.36 | 9.41 | 7.96 | 10.77 | 9.73 | 11.8 | 6.60 | 9.09 |
| Tc/Sr | 0.799 | | 0.748 | | 0.834 | | 0.726 | |

TABLE 7

| | Ratio of $^{99m}$Tc/$^{85}$Sr | | | |
|---|---|---|---|---|
| | EHDP Dose | | | |
| Organ | 0.01 mg/kg | 0.05 mg/kg | 0.1 mg/kg | 0.5 mg/kg |
| Blood | 0.309 | 0.391 | 0.329 | 0.339 |
| Liver | 0.724 | 2.26 | 0.302 | 0.354 |
| Kidney | 2.34 | 6.14 | 2.13 | 2.35 |
| Marrow | 0.780 | 1.33 | 0.478 | 0.579 |
| Femur | 0.786 | 0.734 | 0.834 | 0.705 |
| Tibia | 0.803 | 0.730 | 0.827 | 0.750 |
| Pelvis | 0.851 | 0.806 | 0.892 | 0.770 |
| Spine | 0.758 | 0.722 | 0.773 | 0.674 |
| Ave Bone | 0.799 | 0.748 | 0.834 | 0.726 |
| Muscle | 0.133 | 0.195 | 0.189 | 0.169 |

In all of the above examples, the dosages are based on the weight of the free diphosphonic acid employed to prepare the complex.

The complexes of the present invention are extremely useful for skeletal imaging. They combine the advantages of rapid blood clearance, relatively low soft tissue concentrations and a high degree of in vivo stability against enzymatic and chemical hydrolysis.

Generally, solutions for intravenous administration containing the complexes of the present invention may be prepared with 1–5 ml of $^{99m}$Tc solutions containing 5–100 mCi of activity and can be administered to patients, preferably in a volume of 1–5 ml containing 5–20 mCi of radioactivity.

The dosages administered may range from about 0.01 to about 0.5 mg of complex per kg of body weight, preferably from about 0.01 to 0.02 mg of complex per kg of body weight, based on the weight of the free diphosphonic acid.

What is claimed is:

1. A bone-seeking composition comprising a solution of technetium-99m-tin-methylene diphosphonate complex or technetium-99m-tin-1-aminoethane-1,1-diphosphonate complex in an aqueous medium suitable for intravenous administration.

2. A composition according to claim 1 wherein said diphosphonate is technetium-99m-tin-methylene diphosphonate.

3. A composition according to claim 1 wherein said diphosphonate is technetium-99m-tin-1-aminoethane-1,1-diphosphonate.

* * * * *